United States Patent [19]

Thompson et al.

[11] Patent Number: 5,432,459
[45] Date of Patent: Jul. 11, 1995

[54] LEAKAGE CAPACITANCE COMPENSATING CURRENT SENSOR FOR CURRENT SUPPLIED TO MEDICAL DEVICE LOADS WITH UNCONNECTED REFERENCE CONDUCTOR

[75] Inventors: Richard K. Thompson, Englewood, Colo.; Ernie Sevilla, Herkimer, N.Y.

[73] Assignee: Conmed Corporation, Utica, N.Y.

[21] Appl. No.: 9,598

[22] Filed: Jan. 27, 1993

Related U.S. Application Data

[63] Continuation-in-part of Ser. No. 901,024, Jun. 19, 1992, Pat. No. 5,300,070, which is a continuation-in-part of Ser. No. 853,149, Mar. 17, 1992, abandoned.

[51] Int. Cl.$^6$ ............................................. G01R 19/00
[52] U.S. Cl. ................................... 324/713; 128/908; 606/32
[58] Field of Search ................... 324/158 P, 522, 611, 324/713, 718, 720; 128/908, 639–641; 606/32, 34, 35

[56] References Cited

U.S. PATENT DOCUMENTS

| | | | |
|---|---|---|---|
| 3,946,738 | 3/1976 | Newton et al. | 606/34 |
| 4,094,320 | 6/1978 | Newton et al. | 606/35 |
| 4,437,464 | 3/1984 | Crow | 606/35 |
| 4,532,510 | 7/1985 | Bertrand et al. | 324/611 |
| 5,152,762 | 10/1992 | McElhenney | 606/35 |
| 5,246,439 | 9/1993 | Hebborn et al. | 606/35 |

*Primary Examiner*—Kenneth A. Wieder
*Assistant Examiner*—Christopher M. Tobin
*Attorney, Agent, or Firm*—Larson & Taylor

[57] ABSTRACT

A current sensing device enables sensing the current being delivered from a source to a load at a medical implement connected to the distal end of a primary conductor connected between the source and the load in situations wherein distributed capacitance between the primary conductor and a return path to the source prevents a measurement of current at the source end of the primary conductor from being an accurate measurement of the delivered current. The current sensing device comprises a reference conductor which is located beside and twisted together with the primary conductor along the length thereof but which terminates short of, and is not connected to, the medical implement load, and a subtractor for subtracting the current flowing through the reference conductor from the total load current flowing to the medical implement so as to offset the effect of the distributed capacitance and to thereby produce a current measurement corresponding to the delivered current. The subtractor can comprise a current transformer through which the conductors extend in opposing relation. An integrity detector monitors whether the reference conductor is intact.

12 Claims, 3 Drawing Sheets

LEAKAGE CAPACITANCE COMPENSATING CURRENT SENSOR FOR CURRENT SUPPLIED TO MEDICAL DEVICE LOADS WITH UNCONNECTED REFERENCE CONDUCTOR

CROSS REFERENCES TO RELATED APPLICATION

This application is a continuation-in-part of application Ser. No. 07/901,024, now U.S. Pat. No. 5,300,070 filed on Jun. 19, 1992, and entitled "Electrosurgical Trocar Assembly with Bi-Polar Electrode," which, in turn, is a continuation-in-part of now abandoned application Ser. No. 07/853,149, filed Mar. 17, 1992, and entitled "Electrosurgical Trocar Assembly."

FIELD OF THE INVENTION

The present invention relates to medical systems and instruments wherein electrical current delivered to the load end of electrical cable or other electrical conductor, including but not limited to electrosurgical trocars and r.f. ablation devices, and, more particularly, to current sensor devices for determining the amount of current so delivered.

BACKGROUND OF THE INVENTION

There are a number of instances where it is necessary to determine the amount of current delivered to the distal end of an electrical conductor such as a cable. For example, the above-identified applications, the contents of which are hereby incorporated by reference, disclose an electrosurgical trocar assembly wherein a trocar includes an electrosurgical cutting element connected by a cable to an electrosurgical generator and wherein, in a preferred embodiment, it is desired to shut down the electrosurgical generator when the tip of the trocar penetrates through the wall of the body cavity involved (e.g., the peritoneum). As disclosed in these application, this can be done by sensing the current being delivered by the electrosurgical generator since this delivered current will change when penetration is achieved. Another example of where this is desirable is in connection with r.f. (radio frequency) ablation procedures where there is a need to tightly control delivery of electrosurgical current. The invention will be described below particularly with respect to electrosurgical trocar devices although it is to be understood that the invention is applicable to any situation where there is need to know the amount of a.c. current being delivered to a load at the end of an electrical conductor such as a cable.

Considering the problem to be solved in more detail, when the current being delivered is of high frequency and high voltage as is the current output produced by an electrosurgical generator, a measurement of the total current produced by the generator does not accurately indicate the actual current delivered to the distal end of the electrical connecting cable. The discrepancy or error is due to the distributed capacitance to the current return path of the generator. The current flows through the cable along the entire length thereof and the amount of current flow is determined by the voltage, frequency, distributed capacitance to ground (or return), and cable length. Thus, referring to FIG. 1 wherein an electrosurgical generator is indicated at G, a load impedance (e.g., the impedance of the tissue being operated on by an electrosurgical electrode or cutting element) is indicated at $Z_L$ and a shunt impedance representing the distributed capacitance to ground, i.e., the "leakage" capacitance, is indicated at $Z_{ca}$. The generator voltage is V and thus the total current, $I_t$, can be represented by the equation $I_t = V/Z_{ca} + V/Z_L$. Although the current delivered to the load can be derived by measuring V and $I_t$ and then subtracting out the effect of the capacitance, in many cases, and particularly in electrosurgery, the capacitance is unknown and actually varies with the position of the cable in an unpredictable manner, thereby making a simple current measurement at the generator end of the cable inaccurate.

SUMMARY OF THE INVENTION

In accordance with the invention, a current sensing device is provided which enables accurate measurement of the current actually being delivered from a source to a medical instrument load under circumstances such as that described above wherein a direct measurement of the current at the source side is inaccurate because the effect of distributed capacitance of the connecting cable or other connection between the source and load.

In accordance with a preferred embodiment, a current sensing device is provided for sensing the current delivered from a source to a load formed by a medical implement connected to the distal end of a primary electrical conductor for supplying current to the medical implement load from the source wherein distributed capacitance between the primary conductor and a return path to the source prevents a measurement of current at the source end of the primary conductor from being an accurate measurement of the current actually being delivered to the medical implement load, the current sensing device comprising a reference electrical conductor which is located beside the primary electrical conductor along the length thereof so that the reference conductor is exposed to the same voltage and stray capacitance as the primary conductor but which terminates short of, and is not connected to, the medical implement load, and subtracting means for subtracting the current flowing through said reference conductor from the total load current flowing to the medical implement so as to offset the effect of the distributed capacitance and to thereby produce a current measurement corresponding to the current delivered to the medical implement load.

According to a preferred implementation of this embodiment, the subtracting means comprises a magnetic subtraction arrangement. Advantageously, the magnetic subtraction arrangement comprises a current transformer, the primary conductor extending through the current transformer in a first orientation and the reference conductor extending through current transformer in an opposing orientation so that the output of the current transformer is related to the difference in the current flow through the primary and reference conductors.

Preferably, the current sensing device also includes detector means for sensing whether the reference conductor is intact. In the implementation just described, the detector means preferably comprises a further current transformer for sensing the current flow through the reference conductor.

In a second implementation of the first embodiment, the subtraction means comprises a first impedance connected in series in the primary conductor, a second impedance connected in series in the reference conductor and differential voltage sensing means for sensing the difference in voltage across said first and second impedances. Advantageously, the differential voltage sensing means comprises a first differential amplifier having inputs connected across the first impedance, a second differential amplifier having inputs connected across the second impedance, and a third differential amplifier having inputs connected to the outputs of the first and second operational amplifiers. In this implementation, the detector means for sensing whether the secondary conductor is intact preferably comprises an output connection to the output of the second operational amplifier, i.e., that connected across the second impedance.

In a preferred embodiment, the primary conductor and reference conductor are twisted together or otherwise coupled together along their length.

In accordance with a further embodiment, the current sensing device comprising a current sensor means located at the distal end of the primary conductor for enabling sensing of the current delivered to the medical implement load.

According to yet another embodiment, the current sensing device includes a switch means, connected in series in the primary conductor and located at the load end of the primary conductor for, when opened, enabling a measurement to be made of the resultant voltage when the source is activated, this measurement serving as a reference current level to be subtracted from the current measured when the switch means is closed and a connection is thus completed between the source and the medical implement load.

Other features and advantages of the invention will be set forth in, or apparent from, the following detailed description of preferred embodiments of the invention.

DESCRIPTION OF THE PREFERRED EMBODIMENTS

Figure 2:
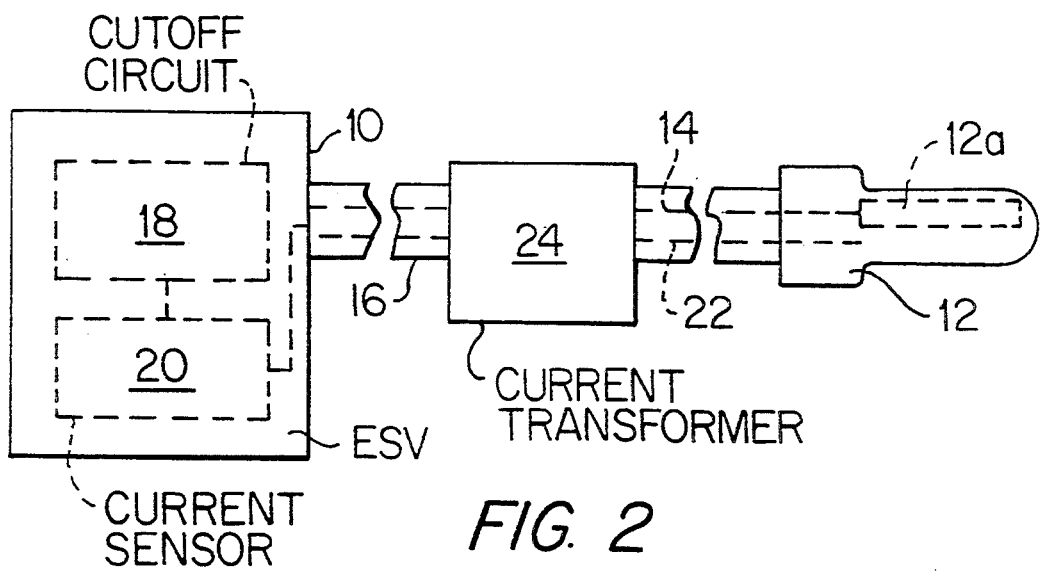
FIG. 2 is a highly schematic block diagram of a first embodiment of the invention.

Referring to FIG. 2, a block diagram is provided of one preferred embodiment of the current sensing device or system of the invention as incorporated in an electrosurgical trocar assembly. The trocar assembly includes an electrosurgical unit or generator (ESU) 10 connected to an electrosurgical trocar 12 such as that disclosed in the above-identified applications through a connecting wire or conductor 14 of a connector cable 16. The ESU 10 includes a shutdown or cutoff circuit 18 which can, for example, correspond to that described in the above-identified applications and which provides for shutdown of the ESU 10, i.e., suspension or cutoff of the power delivered to the trocar 12 from the ESU 10, upon penetration of the trocar tip through the wall of the cavity in question (e.g., the abdominal wall). In this embodiment, a current sensor unit 20 is located with the ESU 10 although a separate control unit or control box could be provided.

As discussed above, an important problem with systems wherein sensing of the current takes place at the ESU (or at a remote control box) is that, at the frequencies involved, the connecting cable 16 presents a sizeable and varying "leakage" impedance that makes detection of the shutoff point difficult. According to the embodiment of FIG. 2 and as is also schematically in FIG. 3 and in FIGS. 4 to 6, a reference wire or conductor 22 is also provided in cable 16 in parallel with, i.e., beside and closely coupled to, the wire 14 carrying the r.f. current to the trocar 12 but is not connected to the cutting element 12a of the trocar 12. As a result, the current sensor 20 can be made to sense the difference between the load conditions seen by the "hot" (primary) wire or conductor 14 and the reference wire or conductor 22.

Figure 1:
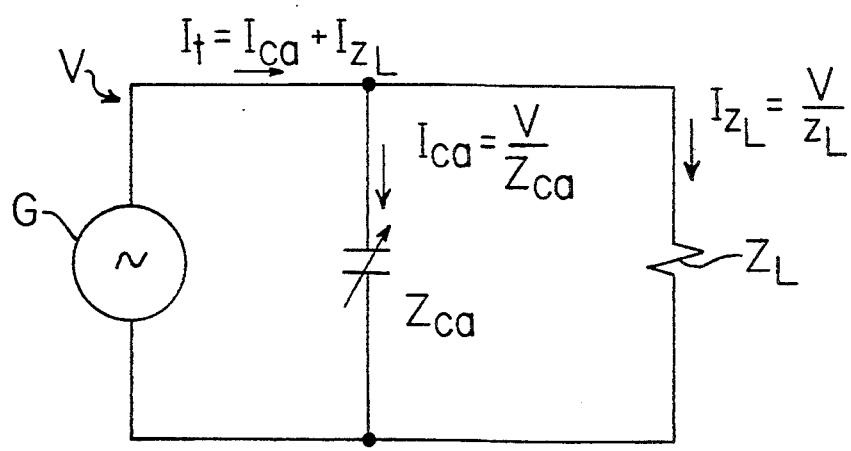
FIG. 1 is, as described above, a schematic circuit diagram illustrating the effect of distributed capacitance on a measurement of the current delivered to a load from a generator.
Figure 3:
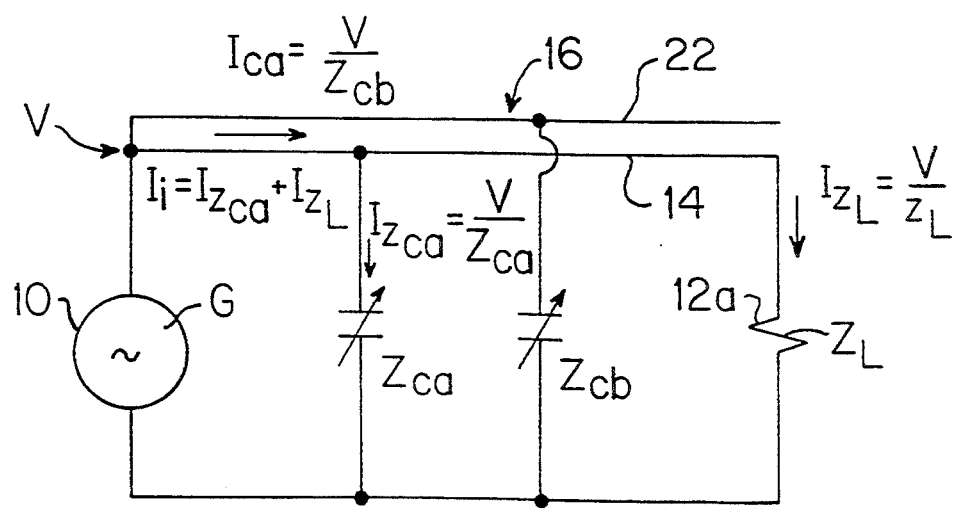
FIG. 3 is a schematic circuit diagram, similar to that of FIG. 1, of the first embodiment of the invention.

As noted above, this arrangement of the reference wire 22 is also shown schematically in FIG. 3, which is a schematic circuit diagram similar to that of FIG. 1 and in which similar notation is used. As illustrated, the second or reference electrical conductor 22 is placed next to the primary or "hot" conductor 14 in such a manner that the current coupled from the reference wire 22 to the current return of the generator 10, other than at the end of the reference wire 22, is equivalent to the current coupled from the primary conductor 14 to the current return of the generator 10. The preferred technique for achieving this is to connect both conductors 14 and 22 to the generator current source and to twist the conductors 14 and 22 together.

As explained above, only the primary electrical conductor 14 is actually connected to a load ($Z_L$) at the distal end, with the secondary conductor terminating just before the load. The secondary or reference conductor 22 will have an impedance to ground, $Z_{cb}$, due to leakage capacitance, i.e., distributed coupling capacitance. The closer the secondary conductor 22 is to the end of conductor 14 the better the current loss through capacitive coupling will match. Because both current losses are made equal, the total current delivered to the tip can be determined, as stated above, by subtracting the leakage current in the secondary wire 22 from the total current in the primary wire 14, i.e., $I_L = I_i - I_{cb}$. Because $I_i$ (the input current which corresponds to the total current $I_t$ above) and $I_{cb}$ can be accurately measured at the generator side of cable 16, if it is ensured that $I_{cb} = I_{ca}$, (or $I_{Z_L}$) can be then ascertained by subtracting $I_{cb}$ from $I_i$.

Figure 4:
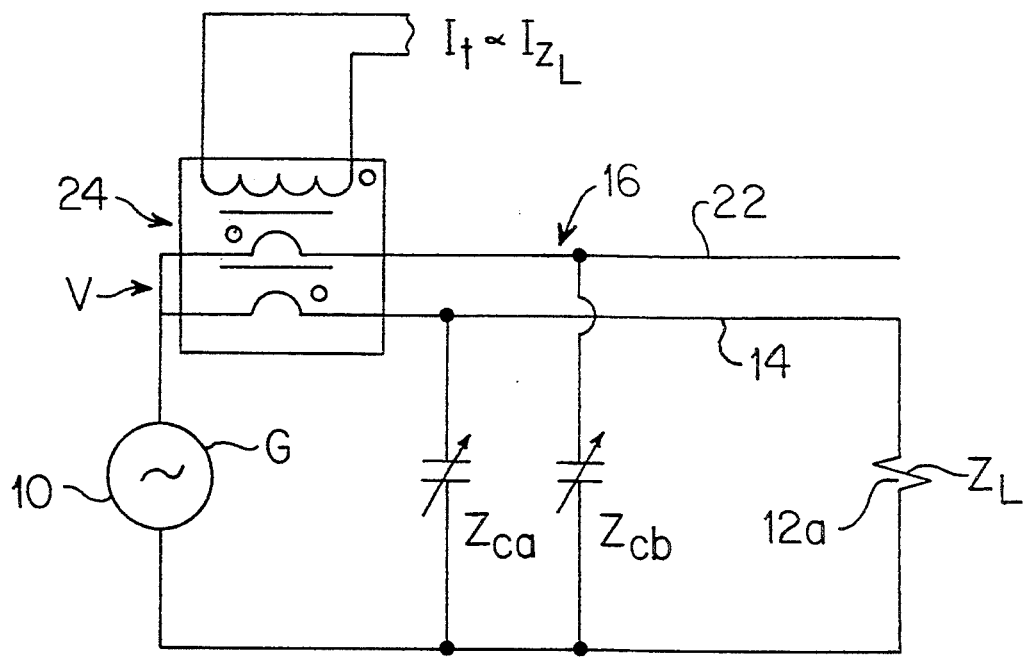
FIG. 4 is a schematic circuit diagram similar to that of FIG. 3, but including a magnetic subtraction arrangement.
Figure 5:
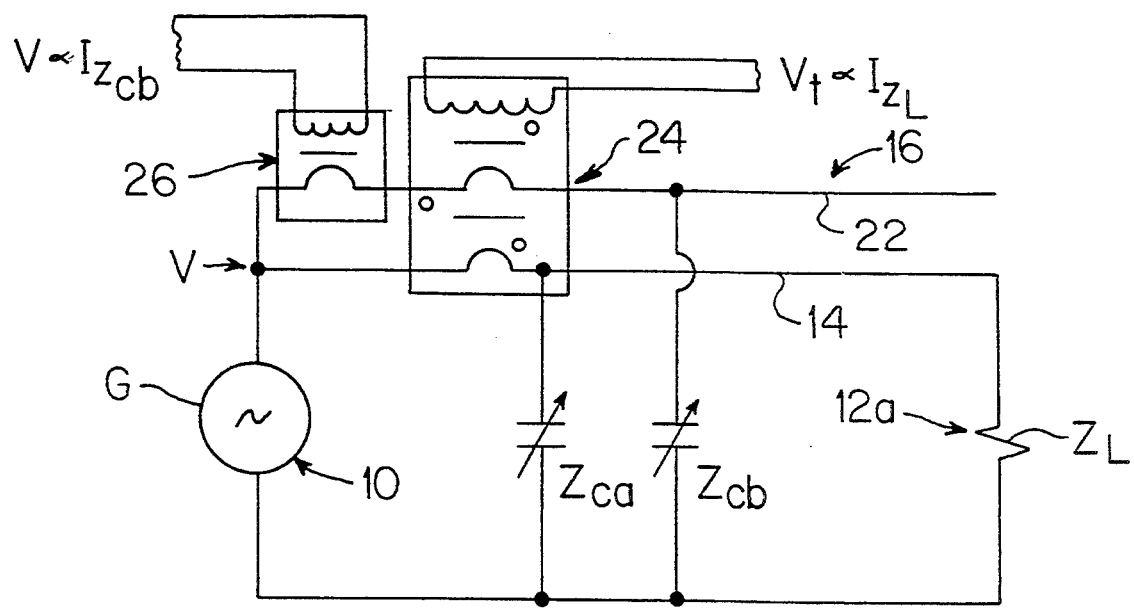
FIG. 5 is a schematic circuit diagram similar to FIG. 4, but including a reference conductor integrity detector.

Several methods can be used to provide the subtraction referred to above, and in the embodiment of FIG. 2, as is illustrated in the schematic circuit diagram of FIG. 4, this can be done by magnetic subtraction, using a current transformer 24. In particular, the primary conductor 14 is placed through the transformer 24 in a given orientation while the secondary or reference conductor 22 is placed through the same transformer 24 in an opposing orientation, as is illustrated in FIG. 4. The output of current transformer 24 will thus be the difference between the current in the primary conductor 14 and the secondary conductor 22, i.e., the current delivered to the load $Z_L$ (cutting element 12a). It is this current that will be sensed by current sensor 20 and used to control cutoff circuit 18, It is noted that if the secondary conductor 16 is broken the current readings will be inaccurate. For this reason, the invention also concerns the provision of techniques to determine whether the secondary conductor 22 is intact. In particular, the controller that senses the current and controls the electrosurgical generator 10 (represented schematically by units 18 and 20 in FIG. 2) is set to produce an alarm signal and to turn off the electrosurgical generator 10 if a minimum level of current in the secondary or reference conductor 22 is not sensed when activation of the ESU 10 is commenced. In the magnetic subtraction embodiment of FIGS. 2 and 4, this is accomplished, as shown in FIG. 5, by adding a further current transformer 26 through which only the secondary conductor 22 passes.

Figure 6:
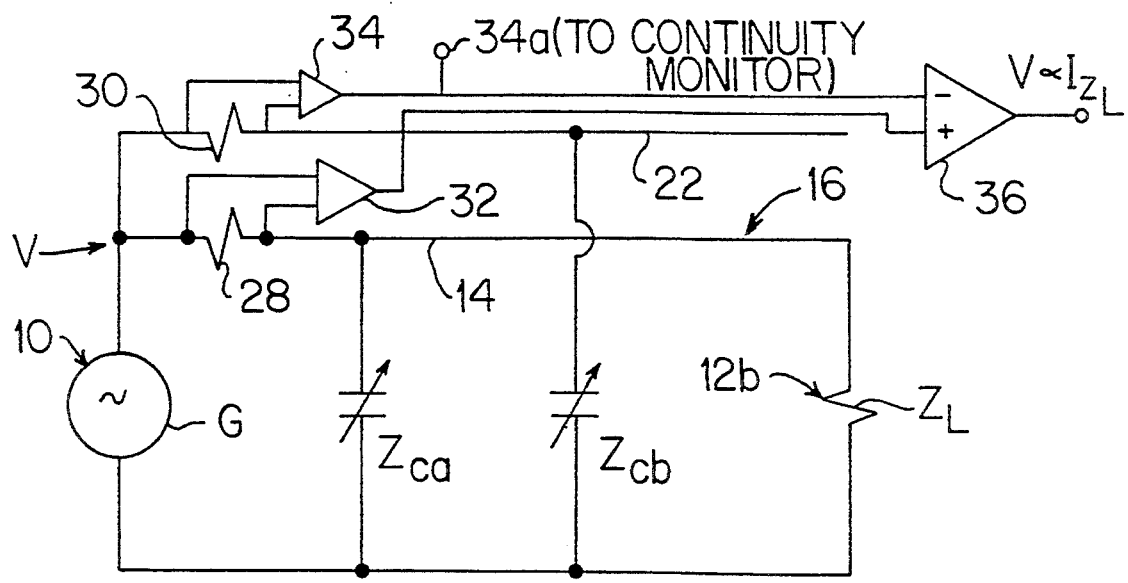
FIG. 6 is a schematic circuit diagram similar to that of FIG. 3 in accordance with a further implementation of the first embodiment of the invention.

A further method of providing the desired current subtraction is illustrated in FIG. 6 which is similar to FIGS. 3 and 4 but in which transformer 24 is replaced by impedances 28 and 30 connected in the respective conductors 14 and 22 Differential voltage amplifiers 32 and 34 are connected across the respective impedances 28 and 30 and the outputs of the two amplifiers are connected to a further differential amplifier 36. Thus, the output of the latter is a voltage $V_o$ proportional to the load current. Monitoring whether conductor 22 is intact can also be achieved with the embodiment of FIG. 5 by, for example, adding an output connection 34a at the output of differential voltage amplifier 34 so as to measure just the voltage across the impedance 30 placed in the secondary conductor 22.

Figure 7:
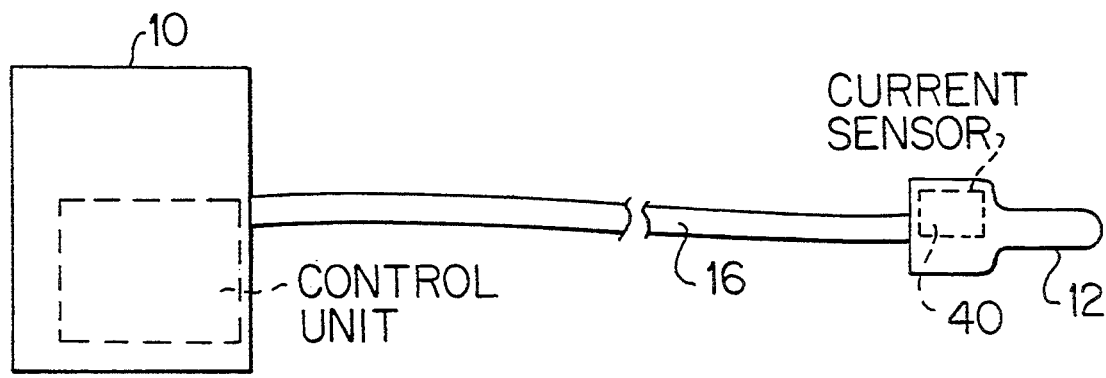
FIG. 7 is a highly schematic block diagram of yet another embodiment of the invention.

Referring to FIG. 7, a further approach to the basic problem discussed above is illustrated. In this embodiment, as is illustrated schematically in FIG. 7, a current sensor 40 is placed at the distal end of the primary or "hot" conductor 14 (there is no reference conductor). If the output of sensor 40 is not affected by capacitance to ground, i.e., where the output is a digital signal, light (through a fiber optic cable), a transmitted r.f. signal or a DC voltage corresponding to current, the load current can be accurately sensed. Any one of a number of different types of current sensors can be used, including a thermal sensor and thermistor (or thermocouple) for converting the signal into a useable voltage, a current transformer with rectification and filtering to convert the current to a DC voltage, and the like.

Figure 8:
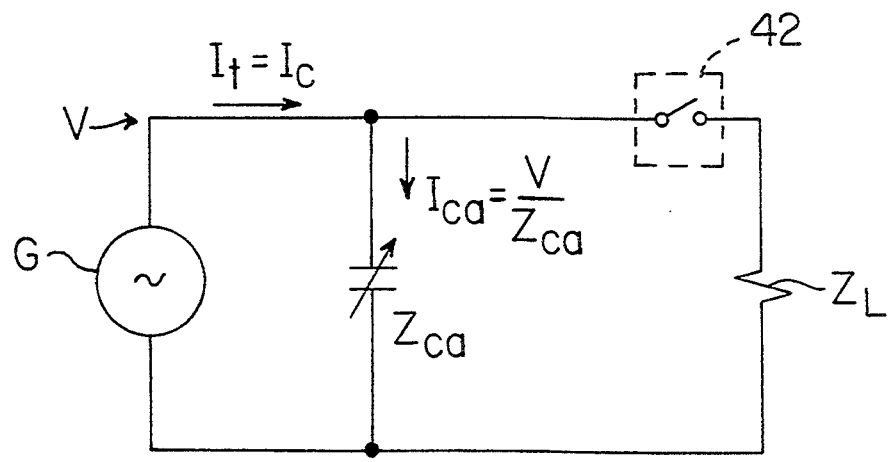
FIG. 8 is a schematic circuit diagram similar to FIG. 1 of a further embodiment of the invention.

Referring to FIG. 8, a further embodiment of the invention is shown. FIG. 8 is similar to FIG. 1 and, again, similar notation has been used. FIG. 8 differs from FIG. 1 in that in order to overcome the problem discussed above, a switching unit or switch 42 is provided at the load end of the cable, i.e., at the end containing load impedance $Z_L$. In operation, the switch 42 is left open thereby forcing the load current to a known zero and the generator G (corresponding to ESU 10 of FIG. 2) is caused to produce voltage. The resulting current can be measured and used as a reference level, assuming that the movement of the connecting cable (e.g., a cable corresponding to cable 16) is minimal, so that the distributed capacitance is constant. This reference current level is subtracted from the total current produced when the switch 42 is activated (closed) and thus current is delivered to the load (and to the distributed capacitance). The result of the open switch measurement can also be used to calculate the distributed capacitance and the resultant calculated value then used to determine the current delivered to the load.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A current sensing device for sensing the A.C. current delivered from a source to a load formed at a medical implement connected to the distal end of a primary electrical conductor for supplying current to the medical implement load from the source wherein distributed capacitance between the primary conductor and a return path to the source prevents a measurement of current at the source end of the primary conductor from being an accurate measurement of the current delivered to the medical implement load, said current sensing device comprising a reference electrical conductor disposed beside the primary electrical conductor along the length thereof but terminating short of, and not being connected to, the medical implement load so that current flowing through the reference electrical conductor is essentially due to distributed capacitance, and subtracting means for subtracting the current flowing through said reference conductor from the current flowing in the primary conductor at the source end so as to offset the effect of the distributed capacitance and to thereby produce a current measurement corresponding to the current delivered to the medical implement load.

2. A current sensing device as claimed in claim 1 wherein said subtracting means comprises a magnetic subtraction arrangement.

3. A current sensing device as claimed in claim 2 wherein said magnetic subtraction arrangement comprises a current transformer, said primary conductor extending through said current transformer in a first orientation and said reference conductor extending through said current transformer in an opposing orientation so that the output of the current transformer is related to the difference in the current flow through the primary and reference conductors.

4. A current sensing device as claimed in claim 1 further comprising detector means for sensing whether said reference conductor is intact.

5. A current sensing device as claimed in claim 4, wherein said detector means comprises a current transformer for sensing the current flow through said reference conductor.

6. A current sensing device as claimed in claim 1 wherein subtraction means comprises a first impedance connected in series in said primary conductor, a second impedance connected in series in said reference conductor and differential voltage sensing means for sensing the difference in voltage across said first and second impedances.

7. A current sensing device as claimed in claim 6 wherein said differential voltage sensing means comprises a first operational amplifier having inputs connected across the first impedance, a second operational amplifier having inputs connected across the second impedance, and a third operational amplifier having inputs connected to the outputs of the first and second operational amplifiers.

8. A current sensing device as claimed in claim 7, further comprising detector means for sensing whether the secondary conductor is intact.

9. A current sensing device as claimed in claim 8 wherein said detector means comprises an output connection to the output of the second operational amplifier connected across said second impedance.

10. A current sensing device as claimed in claim 6 further comprising detector means for sensing whether said second reference detector is intact.

11. A current sensing device as claimed in claim 1 wherein said primary conductor and said reference conductor are twisted together along their length.

12. A current sensing device as claimed in claim 1 wherein said source comprises an electrosurgical generator, said medical implement comprises an electrosurgical electrode, and said primary conductor, said reference conductor and said return path are included in a connector cable connected between said generator and said medical implement.

* * * * *